US005586190A

United States Patent [19]

Trantow et al.

[11] Patent Number: 5,586,190

[45] Date of Patent: Dec. 17, 1996

[54] ACTIVE ADAPTIVE CONTROL SYSTEM WITH WEIGHT UPDATE SELECTIVE LEAKAGE

[75] Inventors: Jerry J. Trantow; Brian M. Finn, both of Madison, Wis.

[73] Assignee: Digisonix, Inc., Middleton, Wis.

[21] Appl. No.: 264,510

[22] Filed: Jun. 23, 1994

[51] Int. Cl.[6] .............................. A61F 11/06; H04B 15/00

[52] U.S. Cl. .................................................. 381/71; 381/94

[58] Field of Search .............................. 381/71, 73.1, 94, 381/93

[56] References Cited

U.S. PATENT DOCUMENTS

| | | | |
|---|---|---|---|
| 4,677,676 | 6/1987 | Eriksson | 381/71 |
| 5,117,401 | 5/1992 | Feintuch | 381/71 |
| 5,206,911 | 4/1993 | Eriksson et al. | 381/71 |
| 5,216,722 | 6/1993 | Popovich | 381/71 |
| 5,278,780 | 1/1994 | Eguchi | 381/71 |
| 5,278,913 | 1/1994 | Delfosse et al. | 381/71 |
| 5,337,366 | 8/1994 | Eguchi et al. | 381/71 |

FOREIGN PATENT DOCUMENTS

| | | | |
|---|---|---|---|
| 6-149266A | 5/1994 | Japan | 381/71 |

OTHER PUBLICATIONS

"Adaptive Filter Theory", Haykin, Prentice-Hall, Englewood Cliffs, New Jersey, 1986, pp. 216–219.

"Adaptive Filter Theory", Second Edition, Haykin, Prentice-Hall, Englewood Cliffs, New Jersey, 1991, pp. 688–689.

"Active Adaptive Sound Control In a Duct: A Computer Simulation", J. C. Burgess, Journal of Acoustic Society of America, 70(3), Sep., 1981, pp. 715–726.

*Adaptive Signal Processing*, B. Widrow and S. D. Stearns, Prentice-Hall, Inc., Englewood Cliffs, NJ, 1985, pp. 376–378.

The Application of Self-Tuning Control Strategies to the Active Reduction of Sound; Doelman and Doppenberg pp. 121–126.

*Primary Examiner*—Edward L. Coles, Sr.
*Assistant Examiner*—Jerome Grant, II
*Attorney, Agent, or Firm*—Andrus, Sceales, Starke & Sawall

[57] ABSTRACT

An active adaptive control system introduces a control signal from an output transducer (14) to combine with the system input signal (6) and yield a system output signal (8). An error transducer (16) senses the system output signal and provides an error signal (44). An adaptive filter model (40) has a model input from a reference signal (42) correlated to the system input signal, and an output outputting a correction signal (46) to the output transducer to introduce the control signal according to a weight update signal (74) provided by the product (from multiplier 72) of the reference signal and the error signal. Selective leakage of the weight update signal is provided in response to a given condition of a given parameter, preferably output power of the correction signal, to control performance of the model, to selectively degrade same according to need. Leakage is varied by multiplying a previous weight update value by a factor $\gamma$ and adding the result to the product of the reference signal and error signal, and varying $\gamma$ as a function of the correction signal.

9 Claims, 2 Drawing Sheets

ACTIVE ADAPTIVE CONTROL SYSTEM WITH WEIGHT UPDATE SELECTIVE LEAKAGE

BACKGROUND AND SUMMARY

The invention relates to active adaptive control systems, and more particularly to an improvement for limiting output power to prevent overdriving of the output transducer.

The invention arose during continuing development efforts relating to the subject matter of U.S. Pat. No. 5,278,913, and co-pending U.S. application Ser. No. 08/166,698, filed Dec. 14, 1993, incorporated herein by reference.

Active acoustic attenuation involves injecting a canceling acoustic wave to destructively interfere with and cancel an input acoustic wave. In an active acoustic attenuation system, the output acoustic wave is sensed with an error transducer, such as a microphone or an accelerometer, which supplies an error signal to an adaptive filter control model which in turn supplies a correction signal to a canceling output transducer or actuator, such as a loudspeaker or a shaker, which injects an acoustic wave to destructively interfere with the input acoustic wave and cancel or reduce same such that the output acoustic wave at the error transducer is zero or some other desired value.

An active adaptive control system minimizes an error signal by introducing a control signal from an output transducer to combine with the system input signal and yield a system output signal. The system output signal is sensed with an error transducer providing the error signal. An adaptive filter model has a model input from a reference signal correlated with the system input signal, an error input from the error signal, and outputs a correction signal to the output transducer to introduce a control signal matching the system input signal, to minimize the error signal. The filter coefficients are updated according to a weight update signal which is the product of the reference signal and the error signal.

The present invention is applicable to active adaptive control systems, including active acoustic attenuation systems.

The present invention addresses the problem of overdriving of the output transducer. Active control solutions sometimes require more actuator power than is available or desirable. Actuators, amplifiers, etc. have limitations that adversely affect control algorithms. Pushed beyond capacity, the control output or power available from the secondary source or output transducer may exhibit saturation, clipping, or otherwise nonlinear behavior. Excessive control effort can result in damaged actuators, excessive power consumption, and instability in the control algorithm.

It is known in the prior art to provide weight update signal leakage to counteract the adaptive process. This is done by implementing an exponential decay of the filter coefficients, intentionally defeating control effort, Widrow and Stearns, *Adaptive Signal Processing*, Prentice-Hall, Inc., Engelwood Cliffs, N.J., 1984, pages 376–378. The exponential decay is typically selected to be slow such that the adaptive process toward a control solution dominates. A deficiency of this method is that it unilaterally, across all power levels, degrades performance. Such leakage is useful for limiting control effort and enhancing numerical stability, but performance suffers because of the lack of consideration for regions where the control effort is in an acceptable range. The present invention addresses and solves this problem.

DETAILED DESCRIPTION

Figure 1:
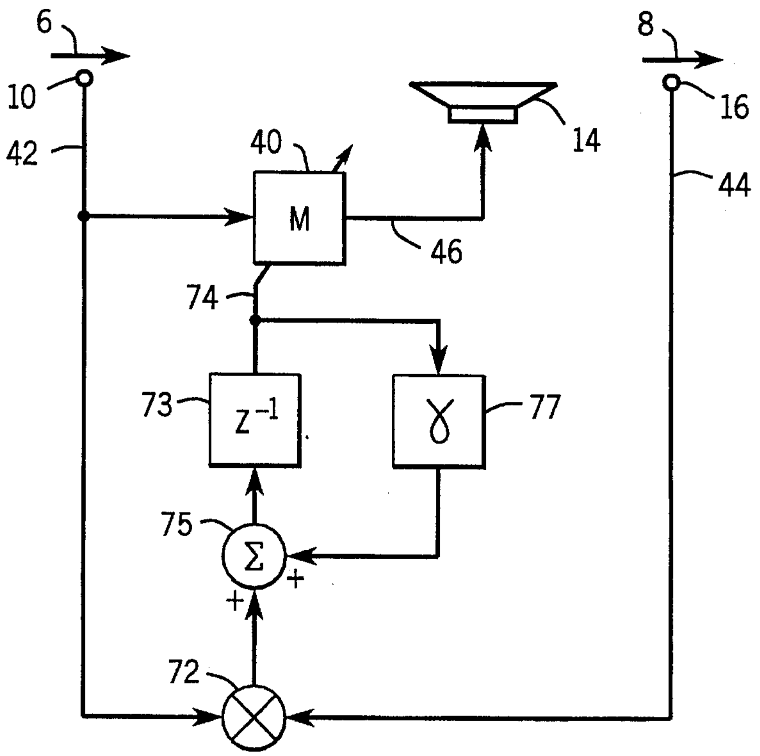
FIG. 1 PRIOR ART
FIG. 1 is a schematic illustration of an active adaptive control system known in the prior art.

FIG. 1 shows an active adaptive control system similar to that shown in U.S. Pat. No. 4,677,676, incorporated herein by reference, and uses like reference numerals therefrom where appropriate to facilitate understanding. The system introduces a control signal from a secondary source or output transducer 14, such as a loudspeaker, shaker, or other actuator or controller, to combine with the system input signal 6 and yield a system output signal 8. An input transducer 10, such as a microphone, accelerometer, or other sensor, senses the system input signal and provides a reference signal 42. An error transducer 16, such as a microphone, accelerometer, or other sensor, senses the system output signal and provides an error signal 44. Adaptive filter model 40 adaptively models the system and has a model input from reference signal 42 correlated to system input signal 6, and an output outputting a correction signal 46 to output transducer 14 to introduce the control signal according to a weight update signal 74. Reference signal 42 and error signal 44 are combined at multiplier 72 to provide the weight update signal through delay element 73. In a known alternative, the reference signal 42 may be provided by one or more error signals, in the case of a periodic system input signal, "Active Adaptive Sound Control In A Duct: A Computer Simulation" J. C. Burgess, Journal of Acoustic Society of America, 70(3), September 1981, pages 715–726, U.S. Pat. Nos. 5,206,911, 5,216,722, incorporated herein by reference.

In updating the filter coefficients, and as is standard, one or more previous weights are added to the current product of reference signal 42 and error signal 44 at summer 75. As noted above, it is known in the prior art to provide exponential decay of all of the filter coefficients in the system. Leakage factor $\gamma$ at 77 multiplies one or more previous weights, after passage through one or more delay elements 73, by an exponential decay factor less than one before adding same at summer 75 to the current product of reference signal 42 and error signal 44, *Adaptive Signal Processing*, Widrow and Stearns, Prentice-Hall, Inc., Engelwood Cliffs, N.J., 1985, pages 376–378, including equations 13.27 and 13.31. As noted above, a deficiency of this method is that it reduces control effort and degrades performance across all power levels, regardless of whether such reduced effort is desired.

Figure 2:
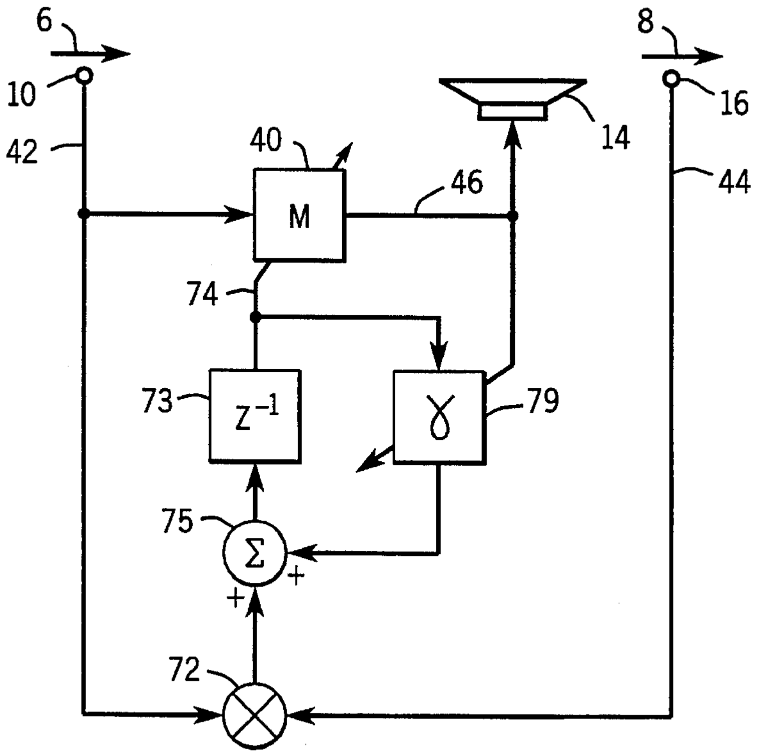
FIG. 2 is a schematic illustration of an active adaptive control system in accordance with the invention.

In the present invention, selective leakage of the weight update signal is provided in response to a given condition of a given parameter, to control performance of the model on an as needed basis. In the preferred embodiment, leakage is varied as a function of correction signal 46. A variable leakage factor $\gamma$ is provided at 79 in FIG. 2, replacing fixed γ 77 of FIG. 1. Leakage factor γ at 79 is varied from a maximum value of 1.0 affording maximum control effort, to a minimum value such as zero providing minimum control effort.

Figure 3:
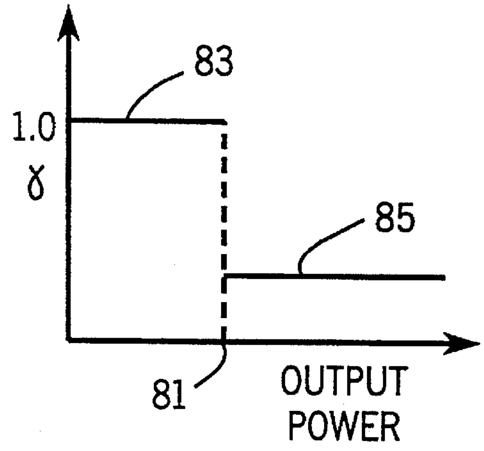
FIG. 3 is a graph showing performance of the system of FIG. 2.
Figure 4:
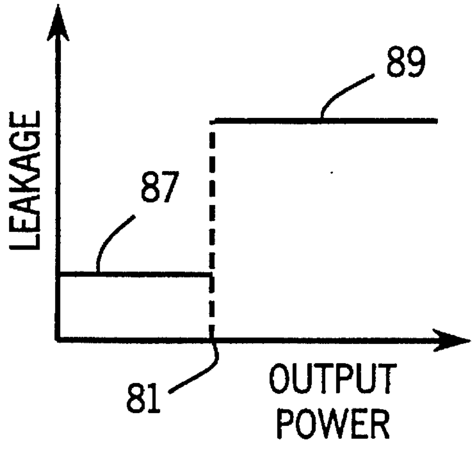
FIG. 4 is a graph further showing performance of the system of FIG. 2.

It is preferred that leakage be varied as a function of the output power of correction signal 46 supplied from the output of model 40 to output transducer 14. In the embodiment in FIG. 3, the leakage is varied as a discontinuous step function of the output power of the correction signal. When the output power exceeds a given threshold at 81, γ is abruptly, nonlinearly changed as a step function from a first level 83 to a second level 85. The reduction at 85 reduces the weight update signal summed at summer 75 with the product of the reference signal 42 and error signal 44 from multiplier 72, and hence reduces the weight update signal supplied to model 40. The noted reduction of γ at threshold 81 increases leakage of the weight update signal, FIG. 4, from level 87 to level 89.

Figure 5:
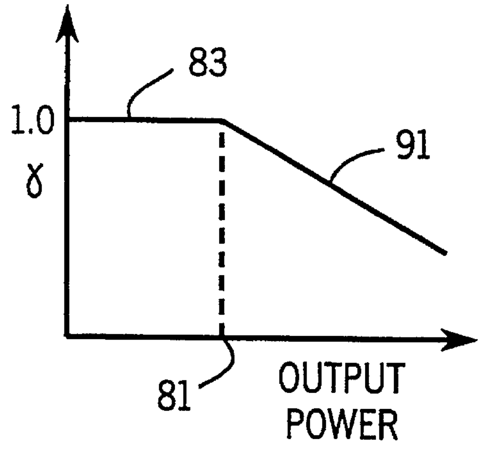
FIG. 5 is a graph showing an alternate performance of the system of FIG. 2.
Figure 6:
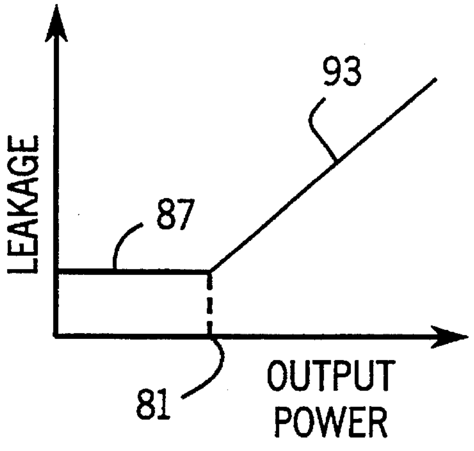
FIG. 6 is a graph further showing alternate performance of the system of FIG. 2.

In another embodiment as shown in FIG. 5, leakage is varied as a continuous function of the output power of the correction signal. In FIG. 5, γ is maintained at level 83 until output power reaches threshold 81, and then is linearly decreased as shown at 91 as a continuous linearly changing value as a function of increasing output power above threshold 81. As shown in FIG. 6, leakage is maintained at level 87 until output power reaches threshold 81, and then is linearly increased at 93 as a continuous linearly changing value as a function of increasing output power above threshold 81.

Other variations of leakage are possible for providing selective leakage of the weight update signal to degrade performance of the model. The leakage is adjustably varied to vary performance of the model by multiplying a previous weight update value by variable γ 79 and adding the result at summer 75 to the product of reference signal 42 and error signal 44 from multiplier 72. γ 79 is varied as a function of correction signal 46, preferably the output power of such correction signal.

It is recognized that various equivalents, alternatives and modifications are possible within the scope of the appended claims.

We claim:

1. An active adaptive control method comprising introducing a control signal from an output transducer to combine with a system input signal and yield a system output signal, sensing said system output signal with an error transducer providing an error signal, providing an adaptive filter model having a model input from a reference signal correlated to said system input signal, and an output outputting a correction signal to said output transducer to introduce said control signal according to a weight update signal, combining said reference signal and said error signal to provide said weight update signal, and providing selective leakage of said weight update signal in response to a given condition of a given parameter, to control performance of said model, and comprising varying said leakage as a discontinuous step function of said correction signal such that when said correction signal exceeds a given threshold, said leakage is abruptly, nonlinearly increased as a step function from a first lower level to a second higher level.

2. An active adaptive control method comprising introducing a control signal from an output transducer to combine with a system input signal and yield a system output signal, sensing said system output signal with an error transducer providing an error signal, providing an adaptive filter model having a model input from a reference signal correlated to said system input signal, and an output outputting a correction signal to said output transducer to introduce said control signal according to a weight update signal, combining said reference signal and said error signal to provide said weight update signal, and providing selective leakage of said weight update signal in response to a given condition of a given parameter, to control performance of said model, and comprising varying said leakage as a continuous increasing function of said correction signal above a given threshold such that when said correction signal exceeds said given threshold, said leakage increases as a continuous function of said correction signal.

3. An active adaptive control method comprising introducing a control signal from an output transducer to combine with a system input signal and yield a system output signal, sensing said system output signal with an error transducer providing an error signal, providing an adaptive filter model having a model input from a reference signal correlated to said system input signal, output outputting a correction signal to said output transducer to introduce said control signal according to a weight update signal, combining said reference signal and said error signal to provide said weight update signal, and providing selective leakage of said weight update signal in response to a given condition of a given parameter, to control performance of said model, and comprising increasing said leakage linearly with increasing output power of said correction signal above a given threshold.

4. An active adaptive control method comprising introducing a control signal from an output transducer to combine with a system input signal and yield a system output signal, sensing said system output signal with an error transducer providing an error signal, providing an adaptive filter model having a model input from a reference signal correlated to said system input signal, and an output outputting a correction signal to said output transducer to introduce said control signal according to a weight update signal, combining said reference signal and said error signal to provide said weight update signal, providing selective leakage of said weight update signal to degrade performance of said model, and adjustably varying said leakage to vary performance of said model, and comprising varying said leakage by multiplying a previous weight update value by a factor γ and adding the result to the product of said reference signal and said error signal, and varying γ as a function of said correction signal, varying γ as a discontinuous step function of said correction signal such that when said correction signal exceeds a given threshold, γ is abruptly, nonlinearly decreased as a step function from a first higher level to a second lower level, to thus abruptly, nonlinearly increase leakage from a first lower level to a second higher level.

5. An active adaptive control method comprising introducing a control signal from an output transducer to combine with a system input signal and yield a system output signal, sensing said system output signal with an error transducer providing an error signal, providing an adaptive filter model having a model input from a reference signal correlated to said system input signal, and an output outputting a correction signal to said output transducer to introduce said control signal according to a weight update signal, combining said reference signal and said error signal to provide said weight update signal, providing selective leakage of said weight update signal to degrade performance of said model, and adjustably varying said leakage to vary performance of said model, and comprising varying said leakage by multiplying a previous weight update value by a factor γ and adding the result to the product of said reference signal and said error signal, and varying $\gamma$ as a function of said correction signal, varying $\gamma$ as a continuous decreasing function of said correction signal above a given threshold such that when said correction signal exceeds said given threshold, $\gamma$ decreases as a continuous function of said correction signal, to thus increase leakage as a continuous function of said correction signal.

6. An active adaptive control method comprising introducing a control signal from an output transducer to combine with a system input signal and yield a system output signal, sensing said system output signal with an error transducer providing an error signal, providing an adaptive filter model having a model input from a reference signal correlated to said system input signal, and an output outputting a correction signal to said output transducer to introduce said control signal according to a weight update signal, combining said reference signal and said error signal to provide said weight update signal, providing selective leakage of said weight update signal to degrade performance of said model, and adjustably varying said leakage to vary performance of said model, and comprising varying said leakage by multiplying a previous weight update value by a factor $\gamma$ and adding the result to the product of said reference signal and said error signal, and varying $\gamma$ as a function of said correction signal, decreasing $\gamma$ linearly with increasing output power of said correction signal above a given threshold, to thus increase leakage linearly with increasing output power of said correction signal above said given threshold.

7. An active adaptive control method comprising introducing a control signal from an output transducer to combine with a system input signal and yield a system output signal, sensing said system output signal with an error transducer providing an error signal, providing an adaptive filter model having a model input from a reference signal correlated to said system input signal, and a model output outputting a correction signal to said output transducer to introduce said control signal according to a weight update signal, adaptively leaking said weight update signal as a function of said correction signal relative to a given threshold to change leakage of said weight update signal when said correction signal exceeds said threshold.

8. The method according to claim 7 comprising adaptively leaking said weight update signal by leaking said weight update signal as a function of said correction signal and supplying the leaked weight update signal to said adaptive filter model to adapt said correction signal controlling leakage of said weight update signal.

9. The method according to claim 8 comprising leaking said weight update signal by multiplying a previous weight update value by a factor $\gamma$ and adding the result to the product of said reference signal and said error signal, and varying $\gamma$ as a function of said correction signal.

* * * * *